United States Patent
Cho et al.

(10) Patent No.: US 7,076,283 B2
(45) Date of Patent: Jul. 11, 2006

(54) DEVICE FOR SENSING CARDIAC ACTIVITY IN AN IMPLANTABLE MEDICAL DEVICE IN THE PRESENCE OF MAGNETIC RESONANCE IMAGING INTERFERENCE

(75) Inventors: Yong Kyun Cho, Maple Grove, MN (US); Ron Kalin, New Hope, MN (US); James D. Reinke, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 202 days.

(21) Appl. No.: 10/004,237

(22) Filed: Oct. 31, 2001

(65) Prior Publication Data
US 2003/0083570 A1    May 1, 2003

(51) Int. Cl.
*A61B 5/05*    (2006.01)
(52) U.S. Cl. .............. 600/410; 600/411; 600/509; 128/901
(58) Field of Classification Search ............... 600/410, 600/409, 422, 423, 411, 508, 509, 521; 607/27, 607/31, 32, 63; 128/901
See application file for complete search history.

(56) References Cited

U.S. PATENT DOCUMENTS

| | | | |
|---|---|---|---|
| 4,091,818 A | 5/1978 | Brownlee et al. | |
| 4,211,235 A | 7/1980 | Keller, Jr. et al. | 128/419 |
| 4,357,943 A | 11/1982 | Thompson et al. | 128/419 |
| 4,379,459 A | 4/1983 | Stein | 128/419 |
| 4,476,868 A | 10/1984 | Thompson | 128/419 |
| 4,539,992 A | 9/1985 | Calfee et al. | 128/419 |
| 4,550,732 A | 11/1985 | Batty, Jr. et al. | 128/419 |
| 4,556,063 A | 12/1985 | Thompson et al. | 128/419 |
| 4,676,248 A | 6/1987 | Berntson | 128/419 |
| 5,052,388 A | 10/1991 | Sivula et al. | 128/419 |
| 5,127,404 A | 7/1992 | Wyborny et al. | 128/419 |
| 5,159,932 A | 11/1992 | Zanetti et al. | 128/696 |
| 5,217,010 A * | 6/1993 | Tsitlik et al. | 607/9 |
| 5,345,362 A | 9/1994 | Winkler | 361/681 |
| 5,522,860 A | 6/1996 | Molin et al. | |
| 5,697,958 A * | 12/1997 | Paul et al. | 607/31 |
| 5,836,975 A | 11/1998 | DeGroot | 607/5 |
| 5,882,304 A * | 3/1999 | Ehnholm et al. | 600/411 |
| 5,904,708 A | 5/1999 | Goedeke | 607/18 |
| 5,964,705 A * | 10/1999 | Truwit et al. | 600/423 |
| 5,989,192 A | 11/1999 | Weijand et al. | 600/504 |
| 6,198,972 B1 | 3/2001 | Hartlaub et al. | 607/63 |
| 6,209,764 B1 | 4/2001 | Hartlaub et al. | 223/94 |
| 6,234,973 B1 | 5/2001 | Meador et al. | 600/486 |
| 6,348,070 B1 * | 2/2002 | Teissl et al. | 623/11.11 |
| 6,424,234 B1 * | 7/2002 | Stevenson | 333/182 |
| 2002/0072769 A1 * | 6/2002 | Silvian et al. | 607/2 |

FOREIGN PATENT DOCUMENTS

| | | |
|---|---|---|
| WO | WO96/41203 | 12/1996 |
| WO | WO99/37370 | 7/1999 |

* cited by examiner

*Primary Examiner*—Ruth S. Smith
(74) *Attorney, Agent, or Firm*—Paul H. McDowall; Girma Wolde-Michael

(57) ABSTRACT

A method is provided, the method comprising detecting a magnetic resonance imaging (MRI) interference signal and enabling at least one preventive measure to protect an implantable medical device from interference by the magnetic resonance imaging (MRI) interference signal. The method also comprises switching from a first sensing mode more affected by the magnetic resonance imaging (MRI) interference signal to a second sensing mode less affected by the magnetic resonance imaging (MRI) interference signal.

8 Claims, 19 Drawing Sheets

DEVICE FOR SENSING CARDIAC ACTIVITY IN AN IMPLANTABLE MEDICAL DEVICE IN THE PRESENCE OF MAGNETIC RESONANCE IMAGING INTERFERENCE

FIELD OF THE INVENTION

This invention relates generally to implantable medical devices and, more particularly, to protecting implantable medical devices from interference by magnetic resonance imaging (MRI) interference signals.

DESCRIPTION OF THE RELATED ART

Since the introduction of the first implantable pacemakers in the 1960s, there have been considerable advances in both the fields of electronics and medicine, such that there is presently a wide assortment of commercially available body-implantable electronic medical devices. The class of implantable medical devices now includes pacemakers, implantable cardioverters, defibrillators, neural stimulators, and drug administering devices, among others. Today's state-of-the-art implantable medical devices are vastly more sophisticated and complex than earlier ones. Today's state-of-the-art implantable medical devices are capable of performing significantly more complex tasks. The therapeutic benefits of such devices have been well proven.

As the functional sophistication and complexity of implantable medical device systems have increased over the years, however, the conventional implantable medical device systems have also been found to be vulnerable to more sophisticated and complex sources of interference. In particular, the conventional implantable medical device systems have been found to be vulnerable to electromagnetic interference signals produced by magnetic resonance imaging (MRI) devices during a magnetic resonance imaging (MRI) scanning session. For example, when a patient having an implantable medical device is subjected to a magnetic resonance imaging (MRI) scanning session, the implantable medical device's sensed voltage signal may be distorted and/or corrupted so that an accurate assessment of the cardiac rhythm and/or function becomes more difficult.

Many conventional implantable medical device systems use atrial/ventricular (A/V) electrograms (voltage measurements using senseamplifiers, for example) for basic cardiac rhythm sensing. During a magnetic resonance imaging (MRI) scanning session, the implantable medical device's sensed atrial/ventricular (A/V) electrograms (voltage measurements) may be distorted and/or corrupted so that an accurate assessment of the cardiac rhythm and/or function becomes more difficult. One conventional approach to coping with the magnetic resonance imaging (MRI) interference is to disable the sensing circuit during the magnetic resonance imaging (MRI) scanning session. However, disabling the sensing circuit necessarily prevents an accurate assessment of the cardiac rhythm and/or function using the sensing circuit. As a result, more sophisticated therapies that may rely on the detection of cardiac activity may not function properly when the sensing circuit has been disabled.

The present invention is directed to overcoming, or at least reducing the effects of, one or more of the problems set forth above.

SUMMARY OF THE INVENTION

In one aspect of the present invention, a method is provided, the method comprising detecting a magnetic resonance imaging (MRI) interference signal and enabling at least one preventive measure to protect an implantable medical device from interference by the magnetic resonance imaging (MRI) interference signal. The method also comprises switching from a first sensing mode more affected by the magnetic resonance imaging (MRI) interference signal to a second sensing mode less affected by the magnetic resonance imaging (MRI) interference signal.

In another aspect of the present invention, a device is provided, the device comprising a detector capable of detecting a magnetic resonance imaging (MRI) interference signal and an actuator capable of enabling at least one preventive measure to protect an implantable medical device from interference by the magnetic resonance imaging (MRI) interference signal. The device also comprises a switch capable of switching from a first sensing mode more affected by the magnetic resonance imaging (MRI) interference signal to a second sensing mode less affected by the magnetic resonance imaging (MRI) interference signal.

In yet another aspect of the present invention, a device is provided, the device comprising means for detecting a magnetic resonance imaging (MRI) interference signal and means for enabling at least one preventive measure to protect an implantable medical device from interference by the magnetic resonance imaging (MRI) interference signal. The device also comprises means for switching from a first sensing mode more affected by the magnetic resonance imaging (MRI) interference signal to a second sensing mode less affected by the magnetic resonance imaging (MRI) interference signal.

BRIEF DESCRIPTION OF THE DRAWINGS

The invention may be understood by reference to the following description taken in conjunction with the accompanying drawings, in which the leftmost significant digit(s) in the reference numerals denote(s) the first figure in which the respective reference numerals appear, and in which:

FIG. 1 schematically illustrates an implantable medical device (IMD) system according to the present invention;

FIG. 2 schematically illustrates a general block diagram of electronic circuitry for the implantable medical device (IMD) system of FIG. 1;

FIG. 3 schematically illustrates a perspective view of one embodiment of the programming unit for the implantable medical device (IMD) system of FIG. 1;

FIG. 4 schematically illustrates a general block diagram of various illustrative embodiments of a device according the present invention comprising a switchable sensing modes, an actuator and a detector;

FIG. 5 schematically illustrates various illustrative embodiments of the device according the present invention as shown in FIG. 4, further comprising a Hall Effect sensor in the detector;

FIG. 6 schematically illustrates various illustrative embodiments of the device according the present invention as shown in FIG. 5, further comprising an atrial/ventricular electrogram (A/V electrogram) in one of the switchable sensing modes and a case switch in the actuator;

FIG. 7 schematically illustrates various illustrative embodiments of the device according the present invention as shown in FIG. 5, further comprising an atrial/ventricular electrogram (A/V electrogram) in one of the switchable sensing modes and a lead isolator in the actuator;

FIG. 8 schematically illustrates various illustrative embodiments of the device according the present invention as shown in FIG. 6, further comprising a can-based accelerometer in the other one of the switchable sensing modes;

FIG. 9 schematically illustrates various illustrative embodiments of the device according the present invention as shown in FIG. 6, further comprising a pressure sensor on a lead in the other one of the switchable sensing modes;

FIG. 10 schematically illustrates various illustrative embodiments of the device according the present invention as shown in FIG. 6, further comprising an accelerometer on a lead in the other one of the switchable sensing modes;

FIG. 11 schematically illustrates various illustrative embodiments of the device according the present invention as shown in FIG. 6, further comprising an accelerometer on a connector block in the other one of the switchable sensing modes;

FIG. 12 schematically illustrates various illustrative embodiments of the device according the present invention as shown in FIG. 6, further comprising a flow sensor in the other one of the switchable sensing modes;

FIG. 13 schematically illustrates various illustrative embodiments of the device according the present invention as shown in FIG. 6, further comprising a heart motion sensor based on time-of-flight in the other one of the switchable sensing modes;

FIG. 14 schematically illustrates various illustrative embodiments of the device according the present invention as shown in FIG. 6, further comprising a temperature sensor in the other one of the switchable sensing modes;

FIG. 15 schematically illustrates various illustrative embodiments of the device according the present invention as shown in FIG. 6, further comprising an impedance-based sensor in the other one of the switchable sensing modes;

FIG. 16 schematically illustrates various illustrative embodiments of the device according the present invention as shown in FIG. 6, further comprising an oxygen sensor in the other one of the switchable sensing modes;

FIG. 17 schematically illustrates various illustrative embodiments of the device according the present invention as shown in FIG. 6, further comprising at least one of a can-based accelerometer, a pressure sensor on a lead, an accelerometer on a lead, an accelerometer on a connector block, a flow sensor, a heart motion sensor based on time-of-flight, a temperature sensor, an impedance-based sensor and/or an oxygen sensor in the other one of the switchable sensing modes;

FIG. 18 schematically illustrates various illustrative embodiments of a method according the present invention; and FIG. 19 schematically illustrates various alternative illustrative embodiments of a method according the present invention.

Figure 1:
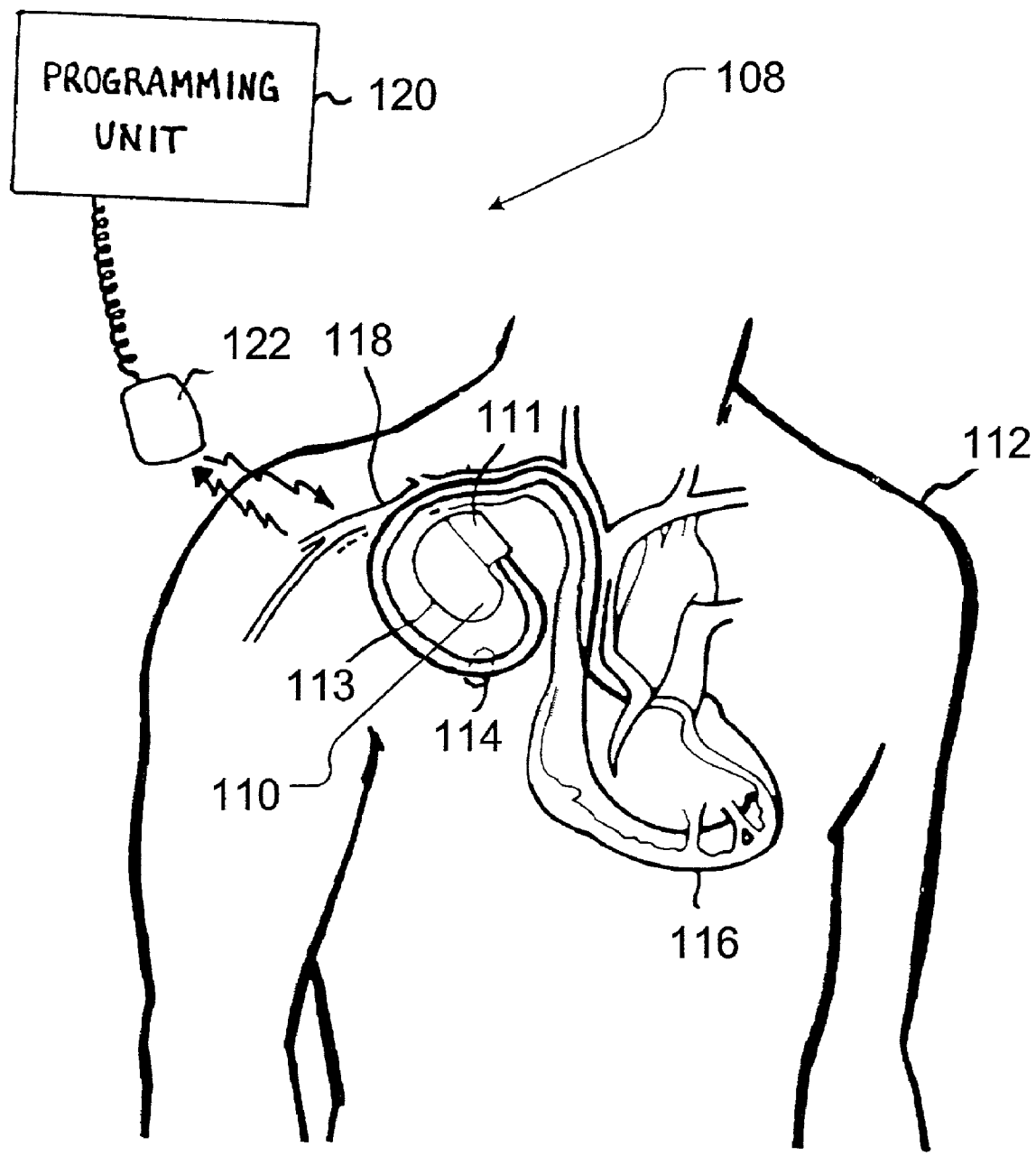
FIGS. 1–19 schematically illustrate various embodiments of a method and a device according to the present invention; and, more particularly.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Illustrative embodiments of an apparatus and a method for operation of the apparatus according to the present invention are shown in FIGS. 1–19. FIG. 1 illustrates an implantable medical device (IMD) system 108, which includes, for example, an implantable pacemaker 110 that has been implanted in a patient 112. The pacemaker 110 is housed within a hermetically sealed, biologically inert outer canister or housing 113 (also known as a can), which may itself be conductive so as to serve as an electrode in the pacemaker's pacing/sensing circuit. One or more pacemaker leads, collectively identified with reference numeral 114 in FIG. 1 are electrically coupled to the pacemaker 110 in a conventional manner and extend into the patient's heart 116 via a vein 118. Disposed generally near a distal end of the leads 114 are one or more exposed conductive electrodes for receiving electrical cardiac signals or delivering electrical pacing stimuli to the heart 116. The leads 114 may be implanted with their distal end situated in either the atrium or ventricle of the heart 116.

Although the present invention is described herein in an embodiment that includes a pacemaker, it may be advantageously embodied in numerous other types of implantable medical device systems which may use circuitry to gather and/or store physiological information from a patient and which may be adversely affected by interference from a magnetic resonance imaging (MRI) device.

FIG. 1 also depicts an external programming unit 120 for non-invasive communication with the implanted device 110 via conventional uplink and downlink communication channels, which are not described in greater detail herein so as to avoid unnecessarily obscuring the instant invention. Associated with the programming unit 120 is a programming head 122, in accordance with conventional medical device programming systems, for facilitating two-way communication between the pacemaker 110 and the programmer 120. In many known implantable device systems, the programming head 122, such as that depicted in FIG. 1, is positioned on the patient's body over the implant site of the device 110 (usually within about 2 to about 3 inches, or equivalently, about 5 to about 8 cm, of skin contact), such that one or more antennas within the head 122 can send radio frequency (RF) signals to, and receive radio frequency (RF) signals from, an antenna (not shown) disposed within the hermetic enclosure of the implanted device 110 or disposed within a connector block 111 of the device 110, in accordance with common practice in the art.

Figure 2:
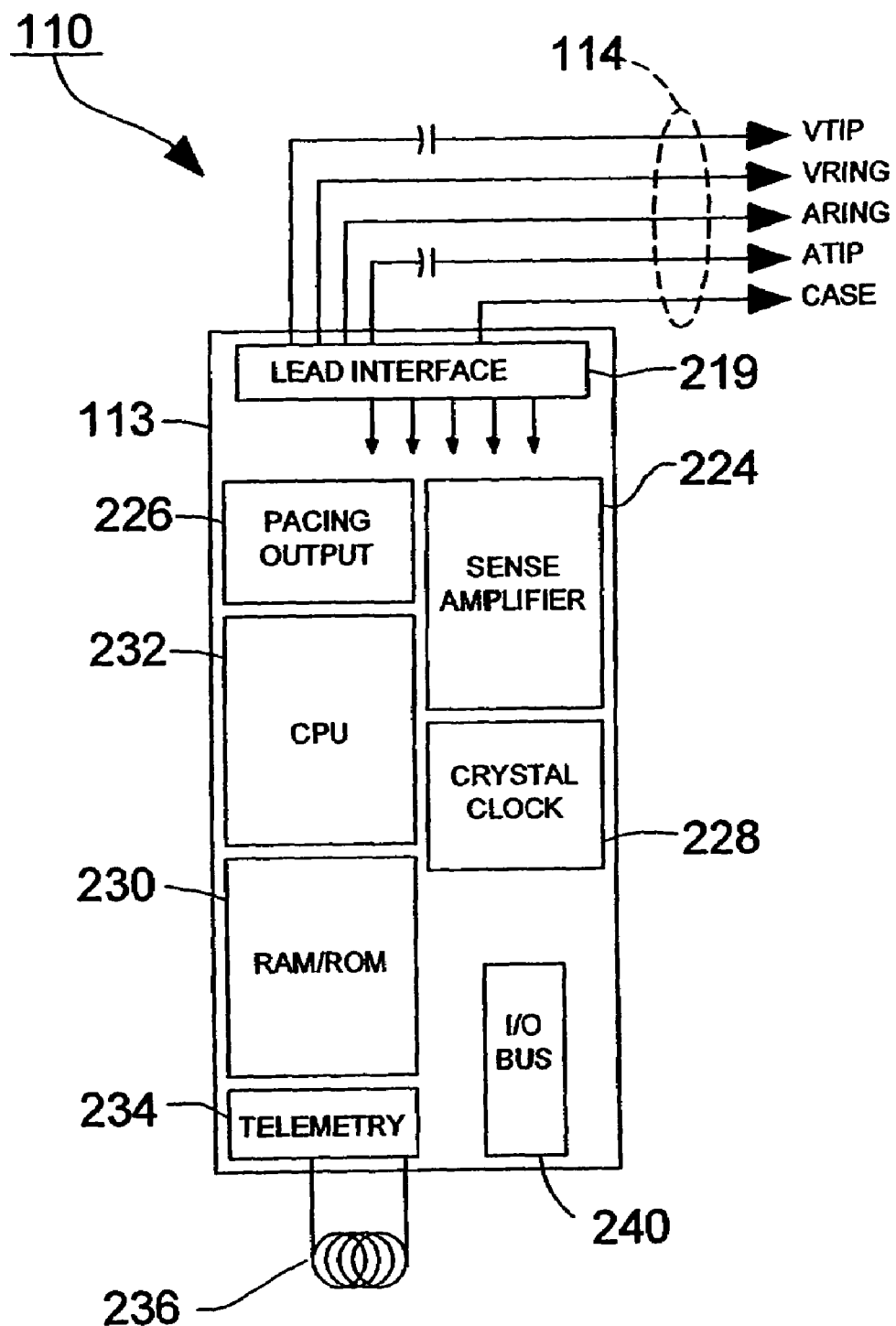

FIG. 2 provides a general block diagram of electronic circuitry that makes up the pacemaker 110. The pacemaker 110 is a device capable of performing a variety of functions, such as delivering electrical stimulation therapy to the patient 112 in accordance with the presently disclosed embodiment of the invention. FIG. 2 shows that pacemaker 110 comprises circuitry for controlling the device's pacing and sensing functions. Aspects of the pacemaker circuitry may be of conventional design, in accordance; for example, with what is disclosed in U.S. Pat. No. 5,052,388 issued to Sivula et al. and entitled "Method and Apparatus for Implementing Activity Sensing in a Pulse Generator." The '388 patent is hereby incorporated by reference herein in its entirety.

To the extent that certain components of the circuitry of the pacemaker 110 are conventional in their design and operation, such components will not be described herein in detail, as it is believed that design and implementation of such components would be a matter of routine practice to those of ordinary skill in the art. For example, the circuitry of the pacemaker 110 shown in FIG. 2 includes sense amplifier circuitry 224, stimulating pulse output circuitry 226, a crystal clock 228, a random-access memory and read-only memory (RAM/ROM) unit 230, and a pacing timing and control circuit in the form of a programmed central processing unit (CPU) 232, all of which are well-known in the art.

The pacemaker 110 also includes an internal telemetry communications circuit 234 coupled to an antenna 236 so that it is capable of communicating with the external programmer/control unit 120. Various telemetry systems for providing the uplink and downlink communication channels between the external programming unit 120 and the implanted pacemaker 110 have been shown in the art and may be employed herein without departing from the spirit and scope of the instant invention. Exemplary communication telemetry systems that may be utilized herein are disclosed, for example, in the following U.S. patents: U.S. Pat. No. 4,539,992 to Calfee et al. entitled "Method and Apparatus for Communicating With Implanted Body Function Stimulator," U.S. Pat. No. 4,550,732 to Batty Jr. et al. entitled "System and Process for Enabling a Predefined Function Within An Implanted Device," U.S. Pat. No. 4,751,589 to Slocum et al. entitled "Biomedical Implant With High Speed, Low Power Two-Way Telemetry," U.S. Pat. No. 4,676,248 to Berntson entitled "Circuit for Controlling a Receiver in an Implanted Device," U.S. Pat. No. 5,127,404 to Wyborny et al. entitled "Telemetry Format for Implanted Medical Device," U.S. Pat. No. 4,211,235 to Keller, Jr. et al. entitled "Programmer for Implanted Device," the above-referenced Markowitz '382 patent and U.S. Pat. No. 4,556,063 to Thompson et al. entitled "Telemetry System for a Medical Device." The Wyborny et al. '404 patent and the Thompson et al. '063 patent are hereby incorporated by reference herein in their respective entireties.

With continued reference to FIG. 2, the pacemaker 110 is coupled to one or more leads 114 which, when implanted, extend transvenously between the implant site of the pacemaker 110 and the patient's heart 116, as previously noted with reference to FIG. 1. Physically, the connections between the leads 114 and the various internal components of the pacemaker 110 are facilitated by a conventional connector block assembly 111, shown in FIG. 1 but not shown in FIG. 2. Electrically, the coupling of the leads 114 and the internal electrical components of the pacemaker 110 may be facilitated by a lead interface circuit 219, which functions, in a multiplexer-like manner, to selectively and dynamically establish necessary connections between various conductors in the leads 114, including, for example, atrial tip and ring electrode conductors ATIP and ARING and ventricular tip and ring electrode conductors VTIP and VRING, and individual electrical components of the pacemaker 110, as would be familiar to those of ordinary skill in the art. For the sake of clarity, the specific connections between the leads 114 and the various components of the pacemaker 110 are not shown in FIG. 2, although it will be clear to those of ordinary skill in the art that, for example, the leads 114 will necessarily be coupled, either directly or indirectly, to sense amplifier circuitry 224 and stimulating pulse output circuitry 226, in accordance with common practice, such that cardiac electrical signals may be conveyed to the sense amplifier circuitry 224, and such that stimulating pulses may be delivered to cardiac tissue, via the leads 114.

It will be appreciated that the signals received over the leads 114 by the sense amplifier circuitry 224 may be collected and stored in the RAM/ROM unit 230 by the CPU 232 acting under control of software and/or firmware also stored in the RAM/ROM unit 230. Additional data, such as the timing of signals delivered by the stimulating pulse output circuitry 226 may also be stored in the RAM/ROM unit 230. This stored data may be later retrieved and delivered to the programming unit 120 via the telemetry communications circuit 234.

As previously noted, the circuitry of the pacemaker 110 includes the central processing unit (CPU) 232 which may be an off-the-shelf programmable microprocessor or microcontroller, but in the presently illustrated embodiment of the invention is a custom integrated circuit. Although specific connections between the CPU 232 and other components of the pacemaker circuitry are not shown in FIG. 2, it will be apparent to those of ordinary skill in the art that the CPU 232 functions to control the timed operation of the stimulating pulse output circuit 226 and the sense amplifier circuit 224 under control of a program of instructions stored in the RAM/ROM unit 230. The crystal clock 228 in the presently illustrated embodiment is a crystal controlled oscillator that provides a main timing clock signal. Again, the lines over which such clock signals are provided to the various components of the pacemaker 110 (e.g., the CPU 232) are omitted from FIG. 2 for the sake of clarity. It is believed that those of ordinary skill in the art will be familiar with such an operative arrangement.

It is to be understood that the various components of the pacemaker 110 depicted in FIG. 2 are powered by means of a battery (not shown), which is contained within the hermetic enclosure of the pacemaker 110, in accordance with common practice in the art. For the sake of clarity in the drawings, the battery and the connections between it and the other components of the pacemaker 110 are not shown.

Stimulating pulse output circuitry 226, which functions to generate cardiac stimuli under control of signals issued by the CPU 232, may be, for example, of the type disclosed in U.S. Pat. No. 4,476,868 to Thompson, entitled "Body Stimulator Output Circuit," which patent is hereby incorporated by reference herein in its entirety. Again, however, it is believed that those of ordinary skill in the art could select from among many various types of prior art pacing output circuits, which would be suitable for the purposes of practicing the present invention.

The sense amplifier circuitry 224, may be, for example, of the type disclosed in U.S. Pat. No. 4,357,943 to Thompson, entitled "Demand Cardiac Pacemaker Having Reduced Polarity Disparity," which patent is hereby incorporated by reference herein in its entirety. Generally, the sense amplifier circuitry 224 functions to receive electrical cardiac signals from the leads 114 and to process such signals to derive event signals reflecting the occurrence of specific cardiac electrical events, including atrial contractions (P-waves) and ventricular contractions (R-waves). These event-indicating signals are provided to the CPU 232 for use by the CPU 232 in controlling the synchronous stimulating operations of the pacemaker 110 in accordance with common practice in the art. In addition, these event-indicating signals, as discussed above, may be communicated, via the uplink communication channel, to the external programming unit 120 for storage and visual display to a physician or clinician.

Those of ordinary skill in the art will appreciate that the pacemaker 110 may include numerous other components and subsystems, for example, activity sensors and associated circuitry. The presence or absence of such additional components in the pacemaker 110, however, is not believed to be directly pertinent to the present invention, which relates generally to the firmware architecture of a portion of the RAM/ROM unit 230, permitting modular feature design for the pacemaker 110, and to the method of operation of this firmware architecture.

Figure 3:
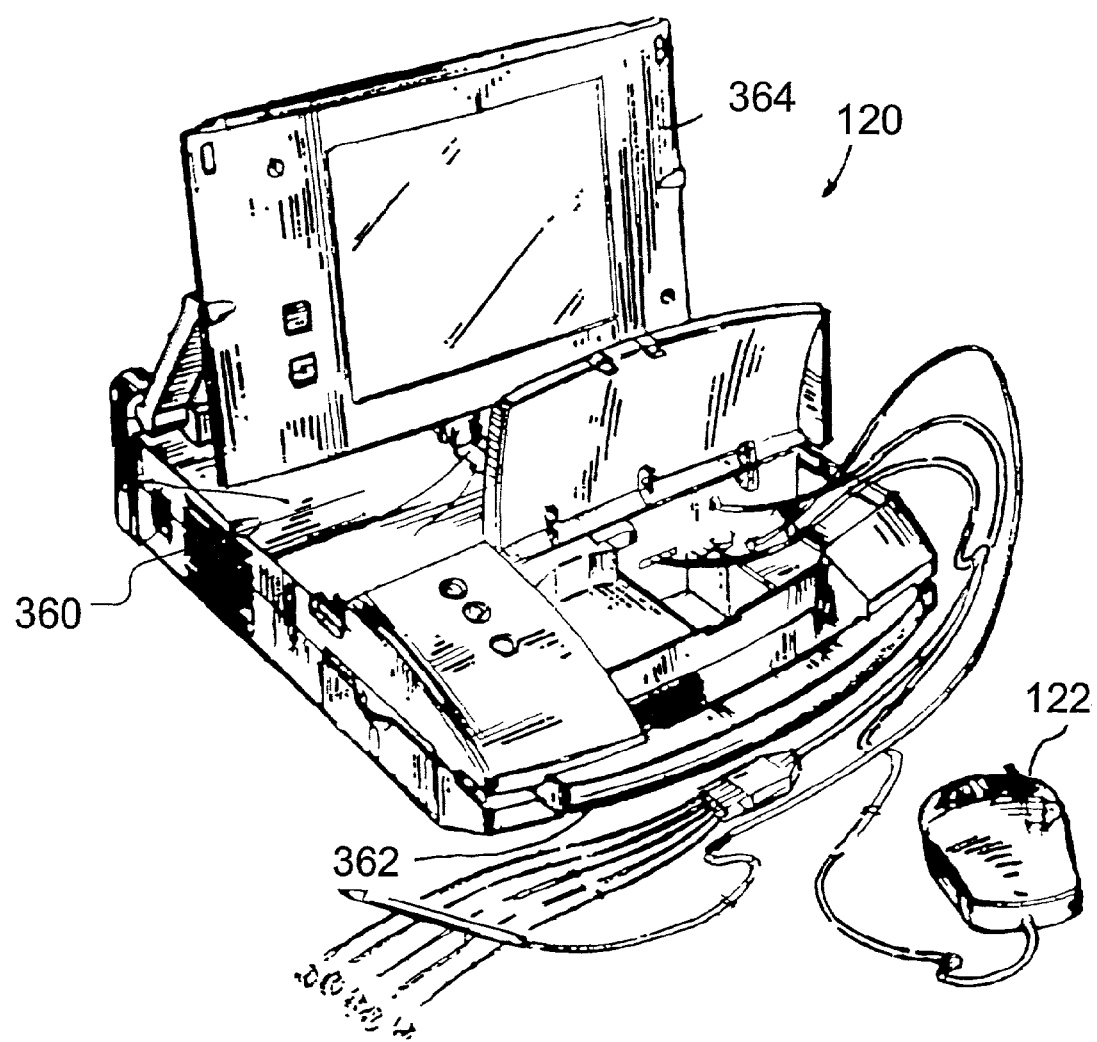

FIG. 3 shows a perspective view of one embodiment of the programming unit 120 in accordance with the presently disclosed embodiment of the invention. Internally, the programmer 120 includes a processing unit (not shown), which in accordance with the presently disclosed embodiment of the invention is a personal computer-type motherboard, for example, a computer motherboard including an Intel 80x86 microprocessor or the like and related circuitry such as digital memory.

Referring to FIG. 3, the programming unit 120 comprises an outer housing 360, which is preferably made of thermal plastic or another suitably rugged yet relatively lightweight material. A carrying handle, designated generally as 362 in FIG. 3, is integrally formed into the front of the housing 360. With the handle 362, the programming unit 120 can be carried like a briefcase.

An articulating display screen 364 is disposed on an upper surface of the housing 60. The display screen 364 folds down into a closed position (not shown) when the programming unit 120 is not in use, thereby reducing the size of the programming unit 120 and protecting the display surface of the display 364 during transportation and storage thereof.

A floppy disk drive is disposed within the housing 360 and is accessible via a disk insertion slot (not shown). A hard disk drive is also disposed within the housing 360, and it is contemplated that a hard disk drive activity indicator (e.g., an LED, not shown) could be provided to give a visible indication of hard disk activation.

As would be appreciated by those of ordinary skill in the art, it is often desirable to provide a means for the programming unit 120 to adapt its mode of operation depending upon the type of implanted device to be programmed. Accordingly, it may be desirable to have an expansion cartridge containing EPROMS or the like for storing program information to control the programming unit 120 to operate in a particular manner corresponding to a given type of implantable device.

In accordance with the presently illustrated embodiment of the invention, the programming unit 120 is equipped with an internal printer (not shown) so that a hard copy of a patient's electrocardiogram (ECG), endocardial electrogram, or of other graphics displayed on the programmer's display screen 364 can be generated.

In the perspective view of FIG. 3, the programming unit 120 is shown with the articulating display screen 364 having been lifted up into one of a plurality of possible open positions such that the display area thereof is visible to a user situated in front of the programming unit 120. The articulating display screen 364 is preferably of the LCD or electro-luminescent type, characterized by being relatively thin as compared, for example, a cathode ray tube (CRT) or the like.

The display screen 364 is operatively coupled to computer circuitry disposed within the housing 360, and is adapted to provide a visual display of graphics and/or data under control of the internal computer.

One embodiment of the programming unit 120 described herein with reference to FIG. 3 is described in more detail in U.S. Pat. No. 5,345,362 issued to Thomas J. Winkler, entitled "Portable Computer Apparatus With Articulating Display Panel," which patent is hereby incorporated herein by reference in its entirety. Also, the Medtronic Model 9760 or 9790 programmers are other implantable device programming units with which the present invention may be advantageously practiced.

Figure 4:
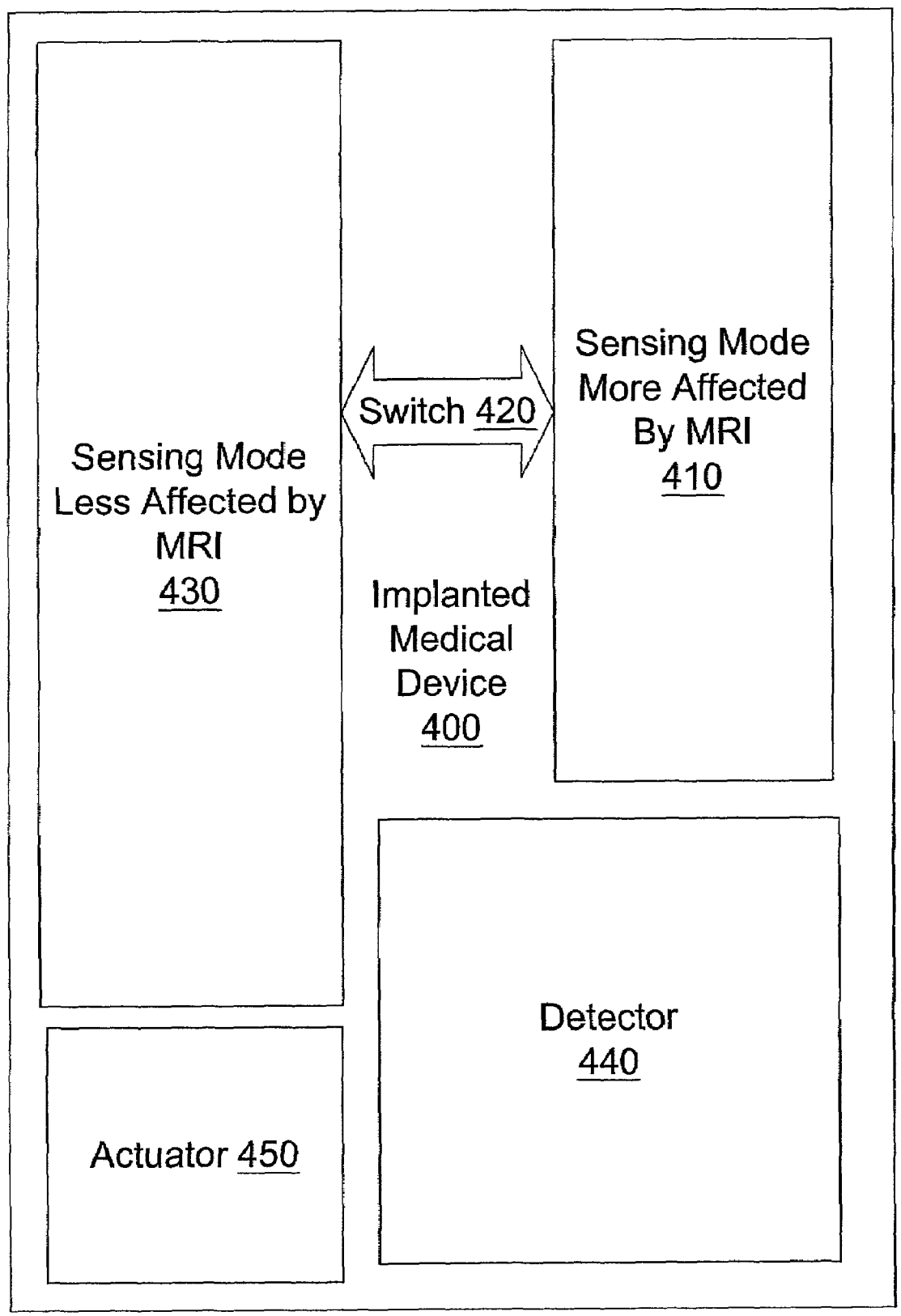
Figure 5:
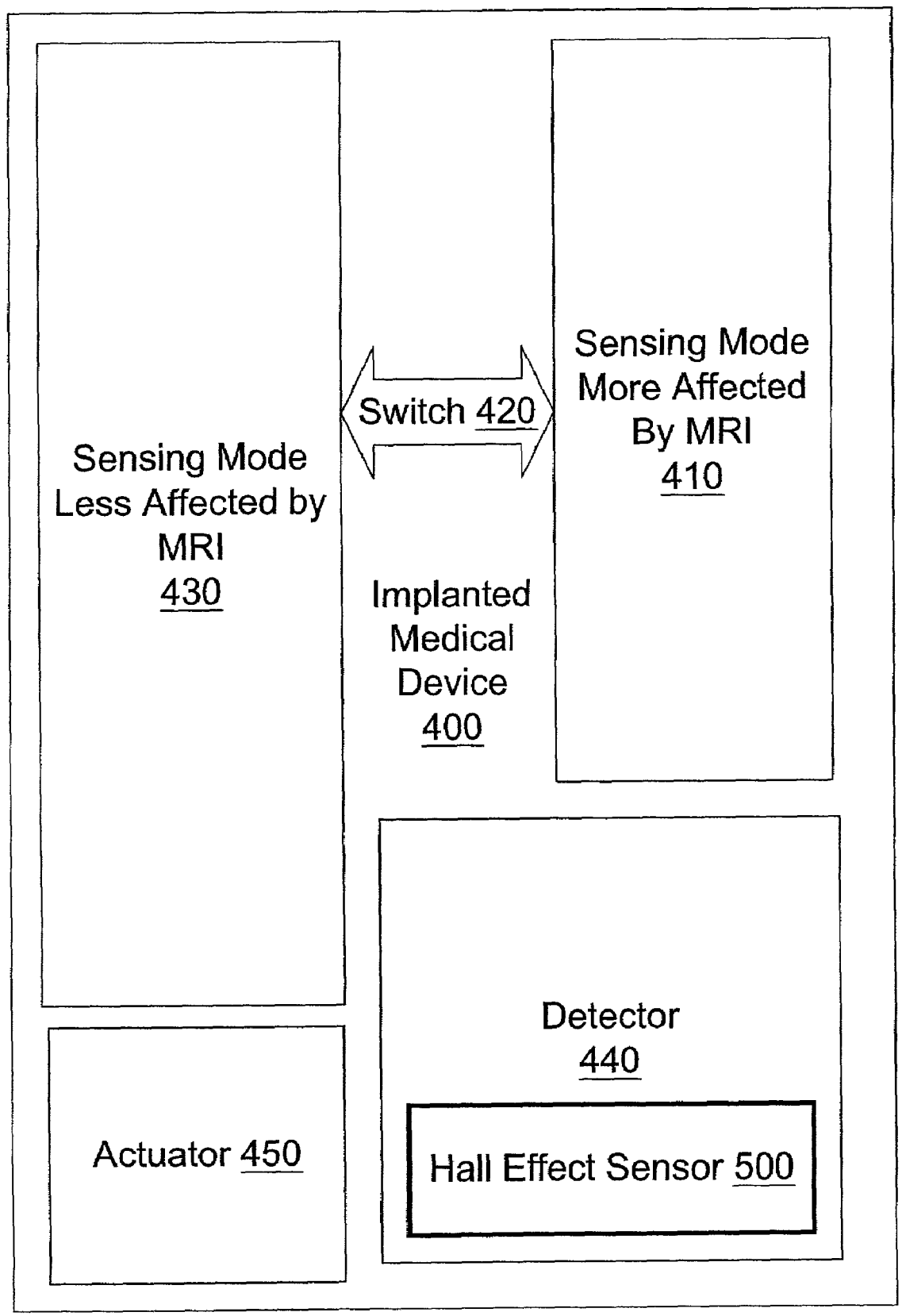

Turning to FIG. 4, a general block diagram of various illustrative embodiments of an implantable medical device 400 according the present invention is shown, the implantable medical device 400 comprising a detector 440 capable of detecting a magnetic resonance imaging (MRI) interference signal, an actuator 450 capable of enabling at least one preventive measure to protect the implantable medical device 400 from interference by the magnetic resonance imaging (MRI) interference signal and a switch 420 capable of switching from a first sensing mode 410 more affected by the magnetic resonance imaging (MRI) interference signal to a second sensing mode 430 less affected by the magnetic resonance imaging (MRI) interference signal. As shown in FIG. 5, the detector 440 may use a Hall Effect sensor 500 to detect the high static magnetic field associated with a magnetic resonance imaging (MRI) scan. The Hall Effect sensor 500 may be capable of detecting magnetic fields having magnetic field strengths in the range of about 0.2 Tesla (2000 Gauss) to about 10 Tesla (100,000 Gauss). A magnetic field having a magnetic field strength above a threshold of about 0.17 Tesla (1700 Gauss) may be taken as an indication of the magnetic resonance imaging (MRI) scan.

Alternatively, and/or additionally, any other type of sensor capable of detecting other properties of the electromagnetic fields that may be produced during the magnetic resonance imaging (MRI) scan may be used by the detector 440 to detect the presence of the high static magnetic field. For example, other fields associated with the MRI scan, such as a static gradient magnetic field, a variable gradient magnetic field with a frequency of up to about 5 kHz, radio-frequency pulses with a frequency of up to about 50 MHz, or a variable magnetic field with a frequency of about 64 MHz, may be detected by the detector 440.

Figure 6:
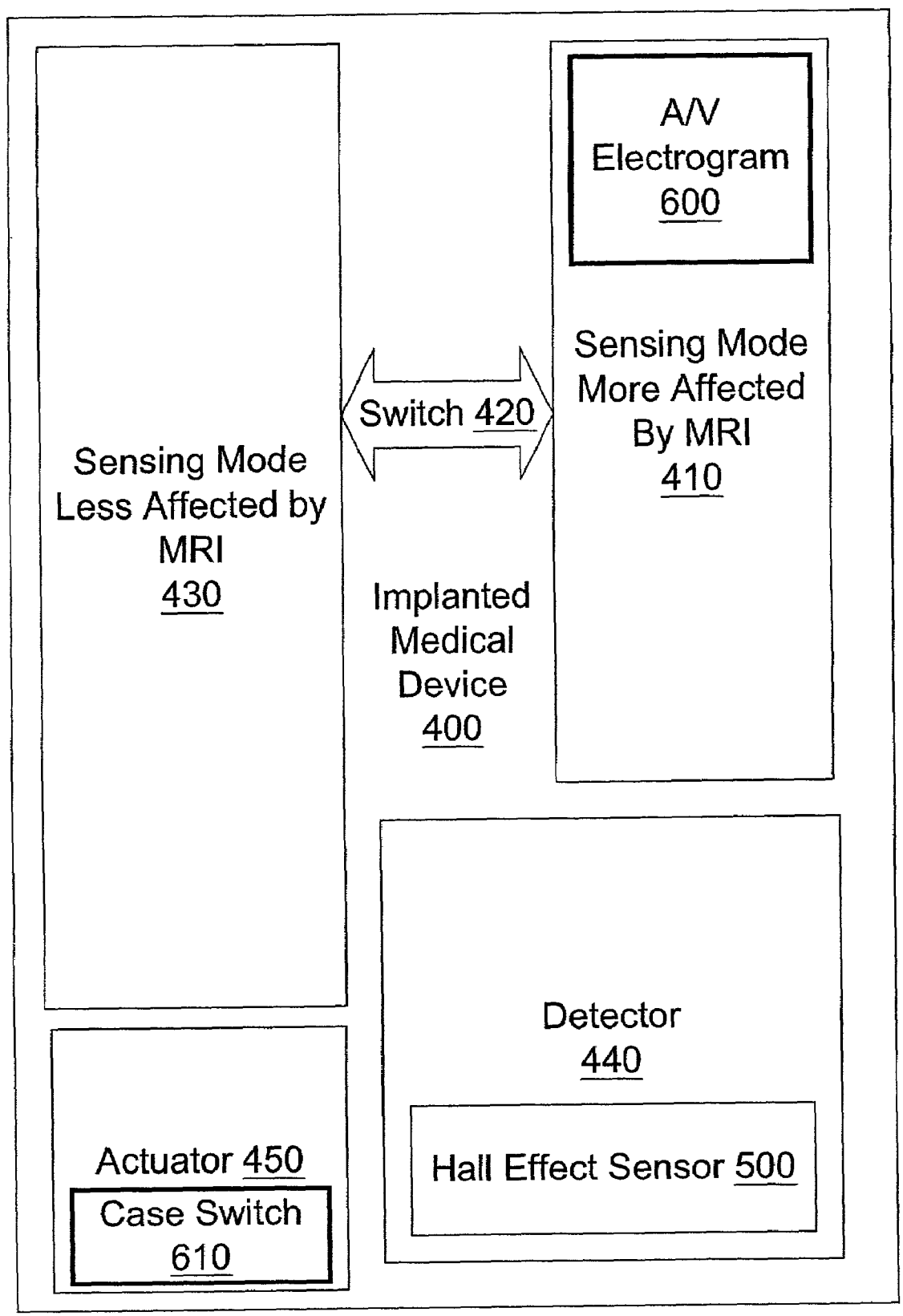

As shown in FIG. 6, the first sensing mode 410 more affected by the magnetic resonance imaging (MRI) interference signal may use a conventional atrial/ventricular electrogram (A/V electrogram) 600 measuring voltages, and/or another type of conventional sense amplifier measuring voltages, for basic cardiac rhythm sensing and/or to assess cardiac rhythm(s). One embodiment of the sense amplifier described herein with reference to FIG. 6 is described in more detail in U.S. Pat. No. 4,379,459 to Stein entitled "Cardiac Pacemaker Sense Amplifier," which patent is hereby incorporated by reference herein in its entirety. The actuator 450 capable of enabling at least one preventive measure to protect the implantable medical device 400 from interference by the magnetic resonance imaging (MRI) interference signal may be capable of opening a case switch 610 for the implantable medical device 400.

Opening the case switch 610 may be performed by the means disclosed in, for example, U.S. Pat. No. 6,209,764 to Hartlaub, entitled "Control of externally induced current in implantable medical devices", which patent is hereby incorporated by reference in its entirety. For another example, opening the case switch 610 may be performed by the means disclosed in U.S. Pat. No. 6,198,972 to Hartlaub, entitled "Control of externally induced current in implantable medical devices," which patent is hereby incorporated by reference in its entirety.

Figure 7:
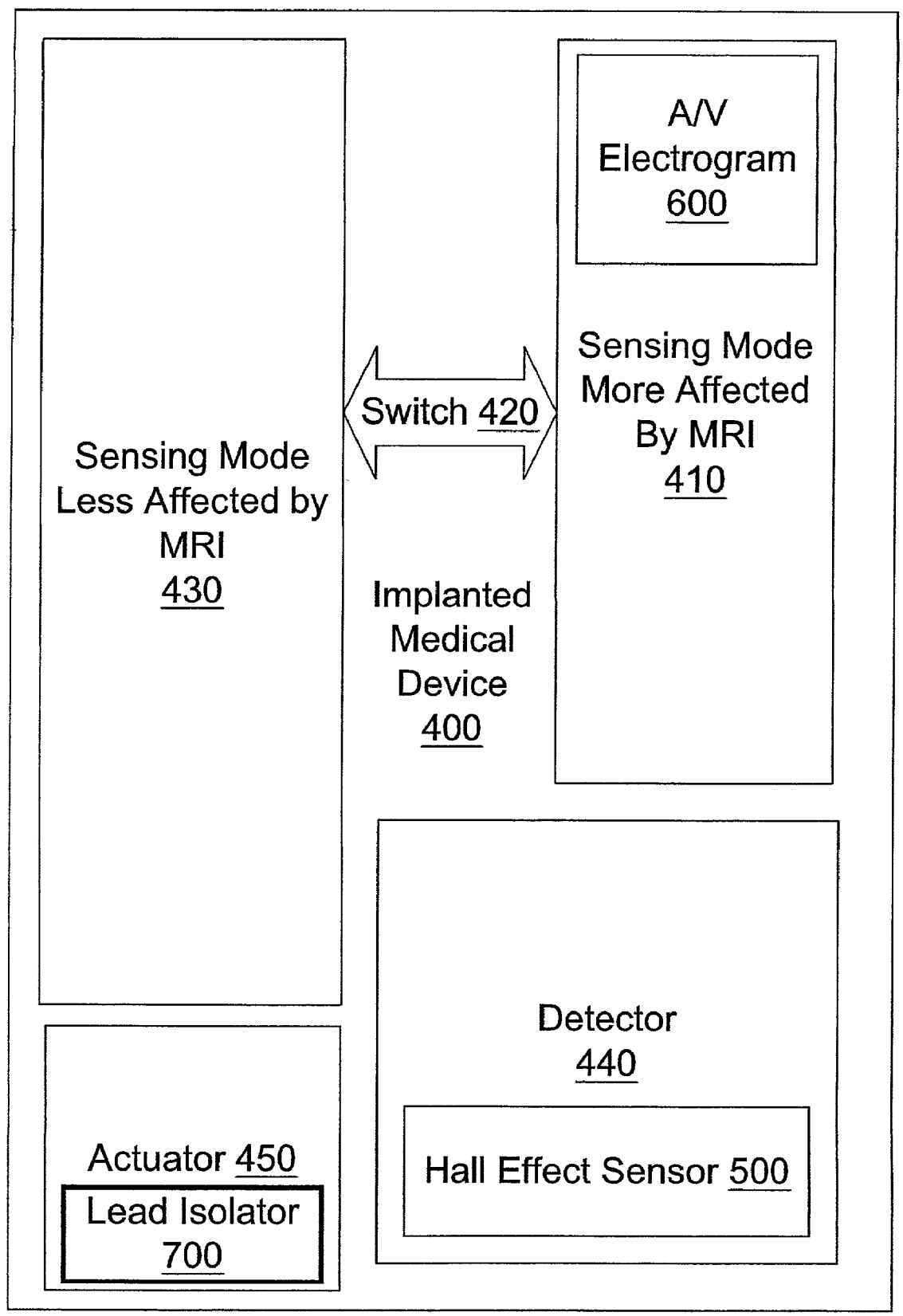

Alternatively, and/or additionally, as shown in FIG. 7, the actuator 450 capable of enabling at least one preventive measure to protect the implantable medical device 400 from interference by the magnetic resonance imaging (MRI) interference signal may be capable of electrically isolating one or more of the leads 114 (FIG. 1) from the can 113. This may be accomplished using a lead isolator 700, for example. Electrically isolating the leads from the can reduces eddy current flows induced by the magnetic fields associated with the magnetic resonance imaging (MRI) scan.

Figure 17:
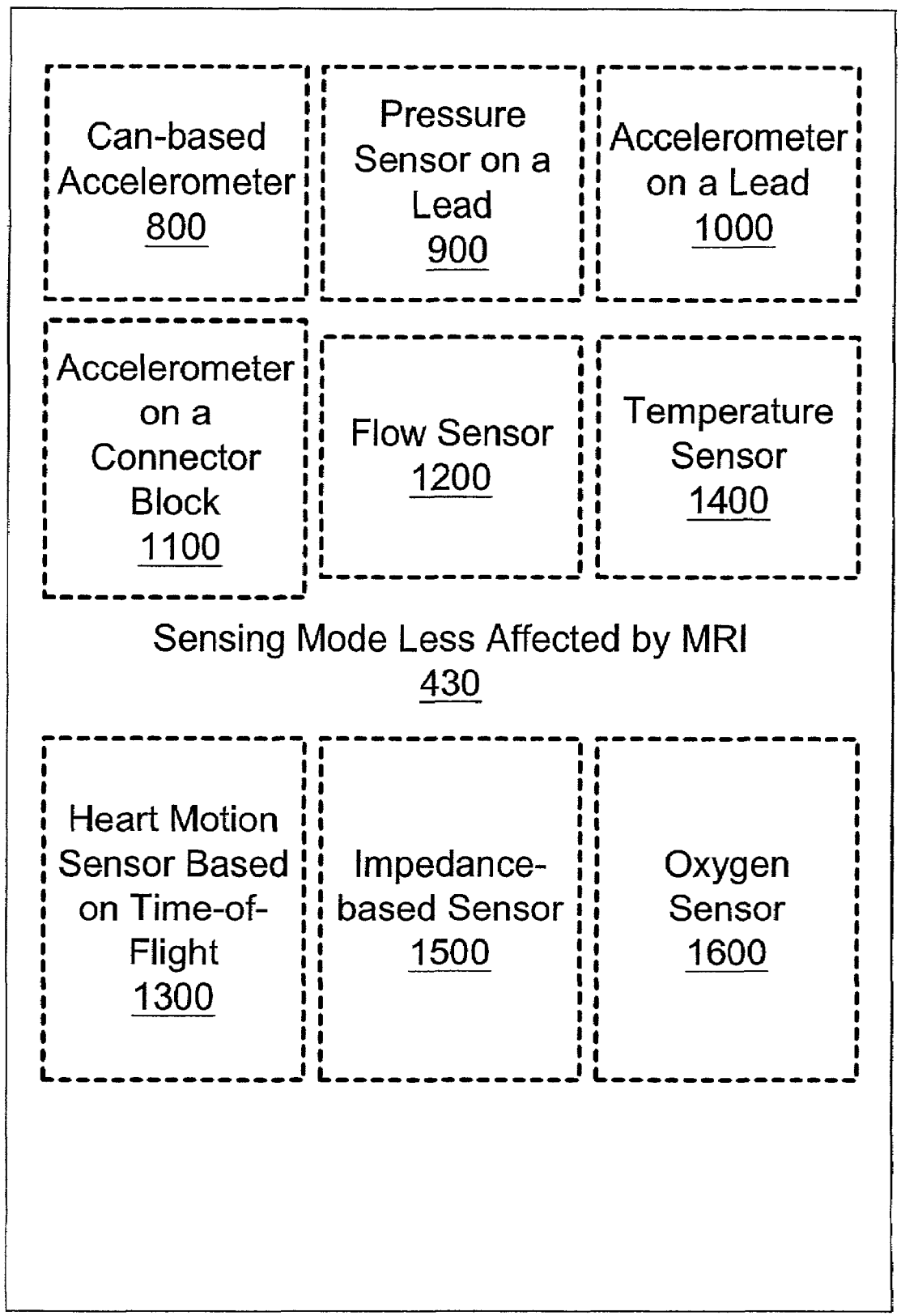

As shown in FIGS. 8–16, the second sensing mode 430 less affected by the magnetic resonance imaging (MRI) interference signal may use at least one of a can-based accelerometer 800 (FIG. 8), a pressure sensor on a lead 900 (FIG. 9), an accelerometer on a lead 1000 (FIG. 10), an accelerometer on a connector block 1100 (FIG. 11), a flow sensor 1200 (FIG. 12), a heart motion sensor 1300 based on time-of-flight (FIG. 13), a temperature sensor 1400 (FIG. 14), an impedance-based sensor 1500 (FIG. 15) and/or an oxygen sensor 1600 (FIG. 16) for basic cardiac rhythm sensing and/or to assess cardiac rhythm(s). As shown in FIG. 17, the second sensing mode 430 may use one or more of the can-based accelerometer 800, the pressure sensor on a lead 900, the accelerometer on a lead 1000, the accelerometer on a connector block 1100, the flow sensor 1200, the heart motion sensor 1300 based on time-of-flight, the temperature sensor 1400, the impedance-based sensor 1500 and/or the oxygen sensor 1600, each indicated in phantom, substantially simultaneously and/or sequentially as appropriate, for basic cardiac rhythm sensing and/or to assess cardiac rhythm(s).

Figure 8:
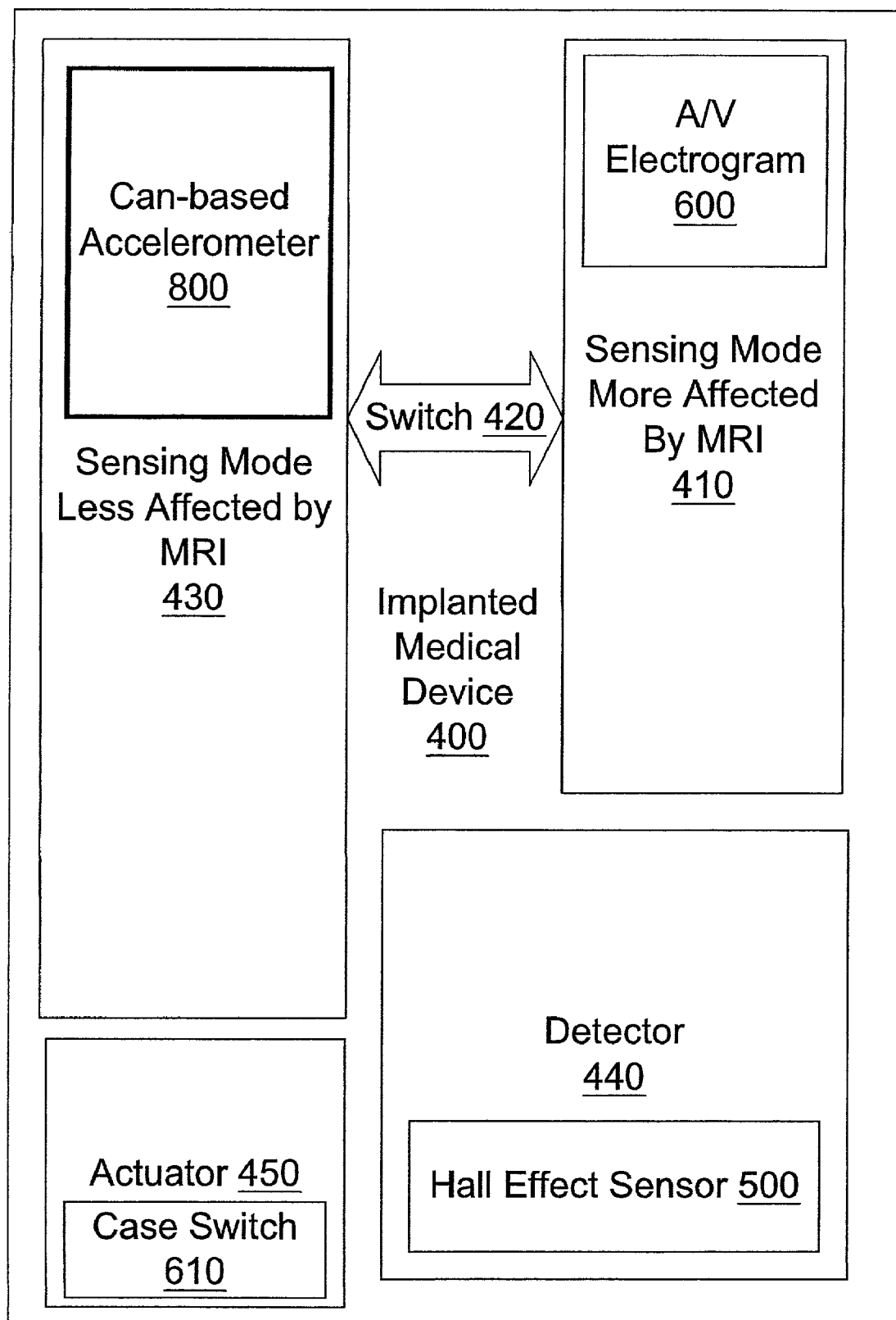
Figure 9:
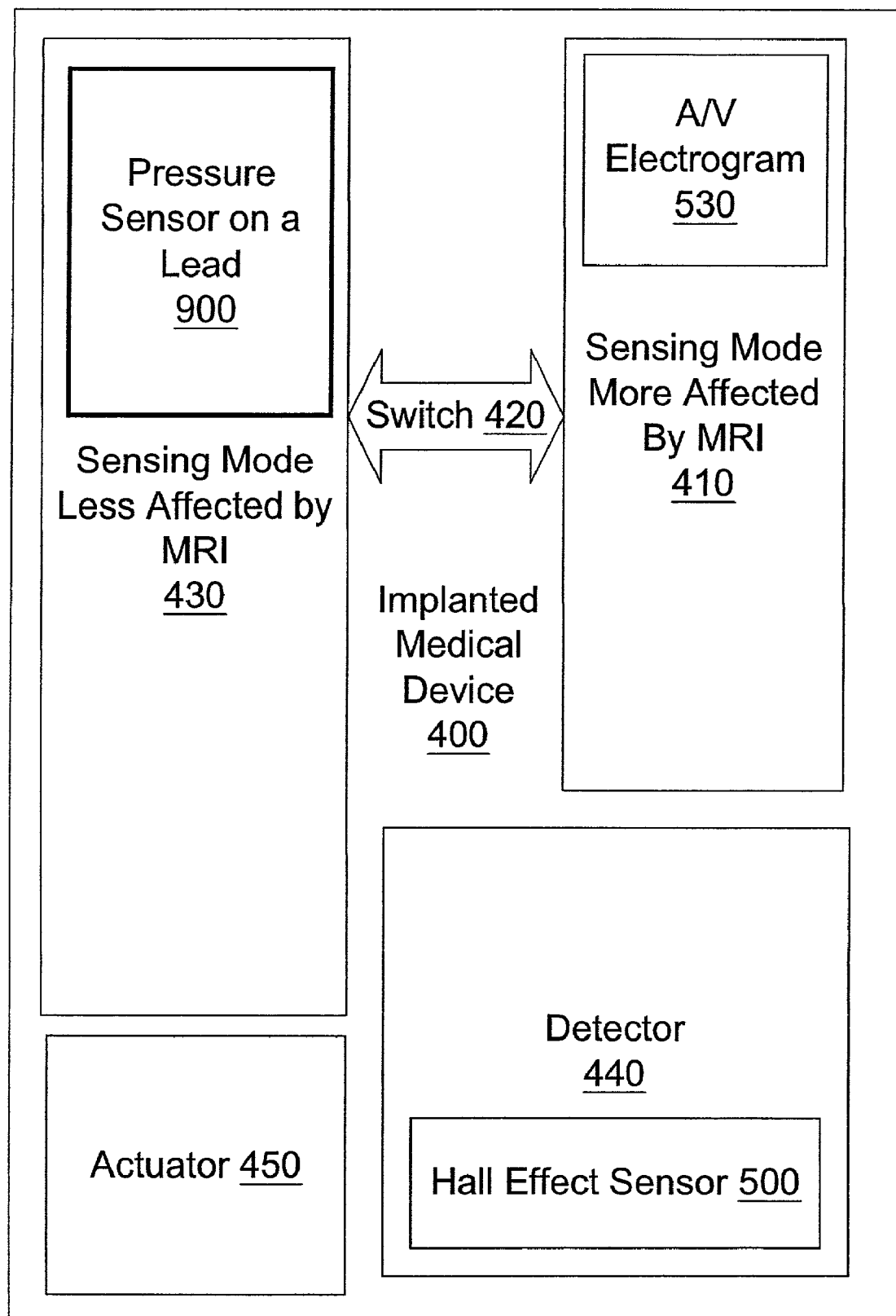
Figure 10:
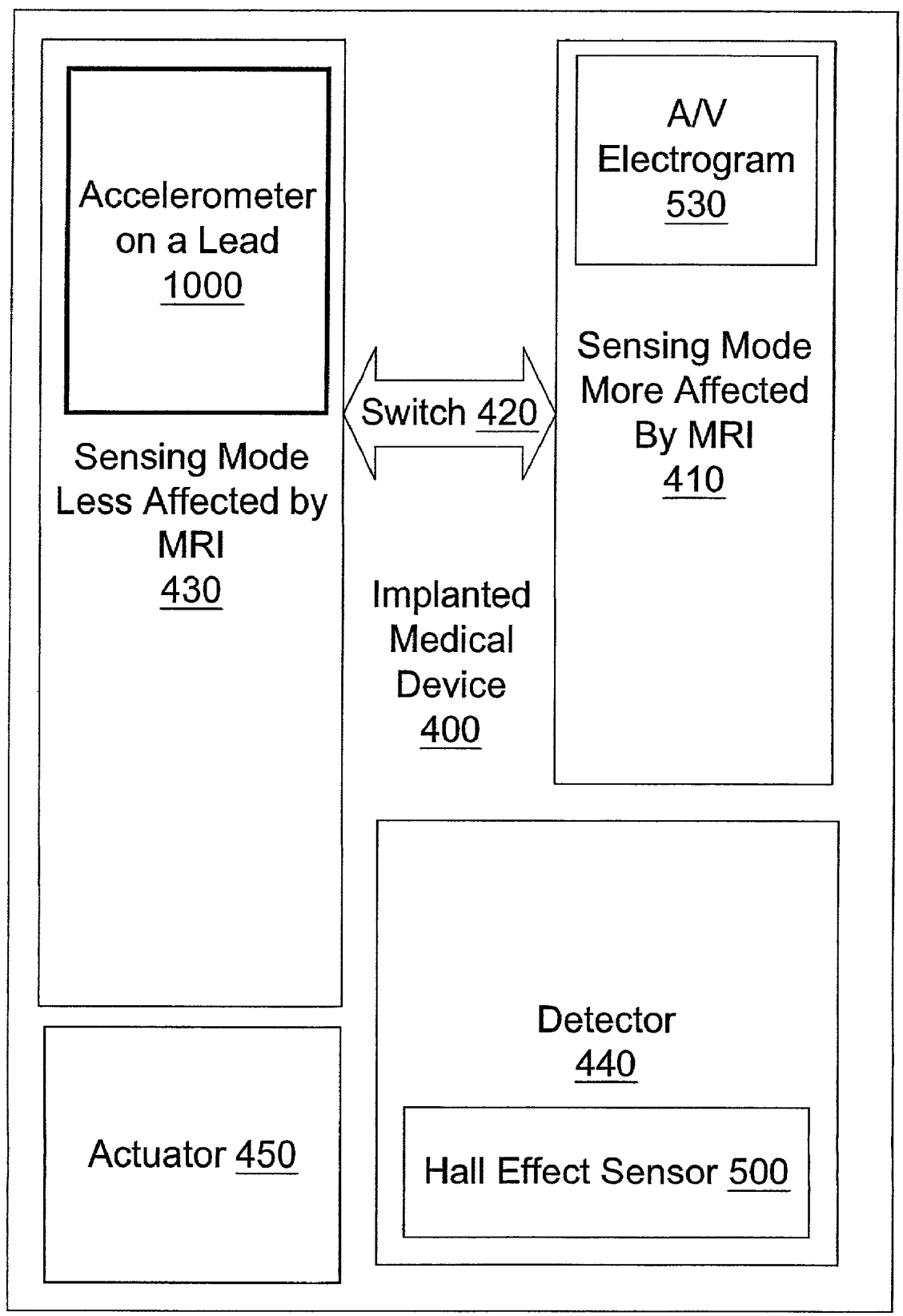
Figure 11:
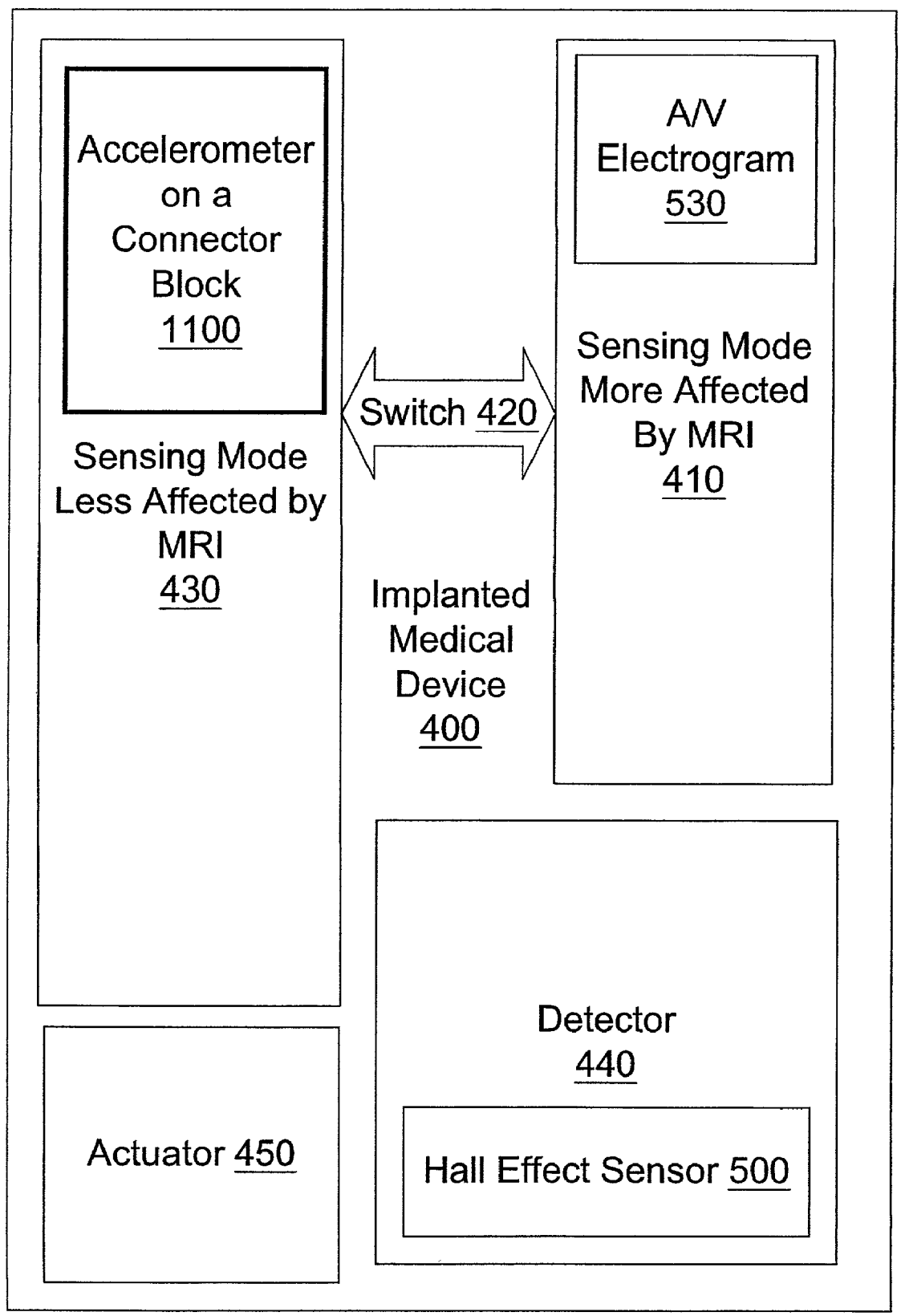
Figure 12:
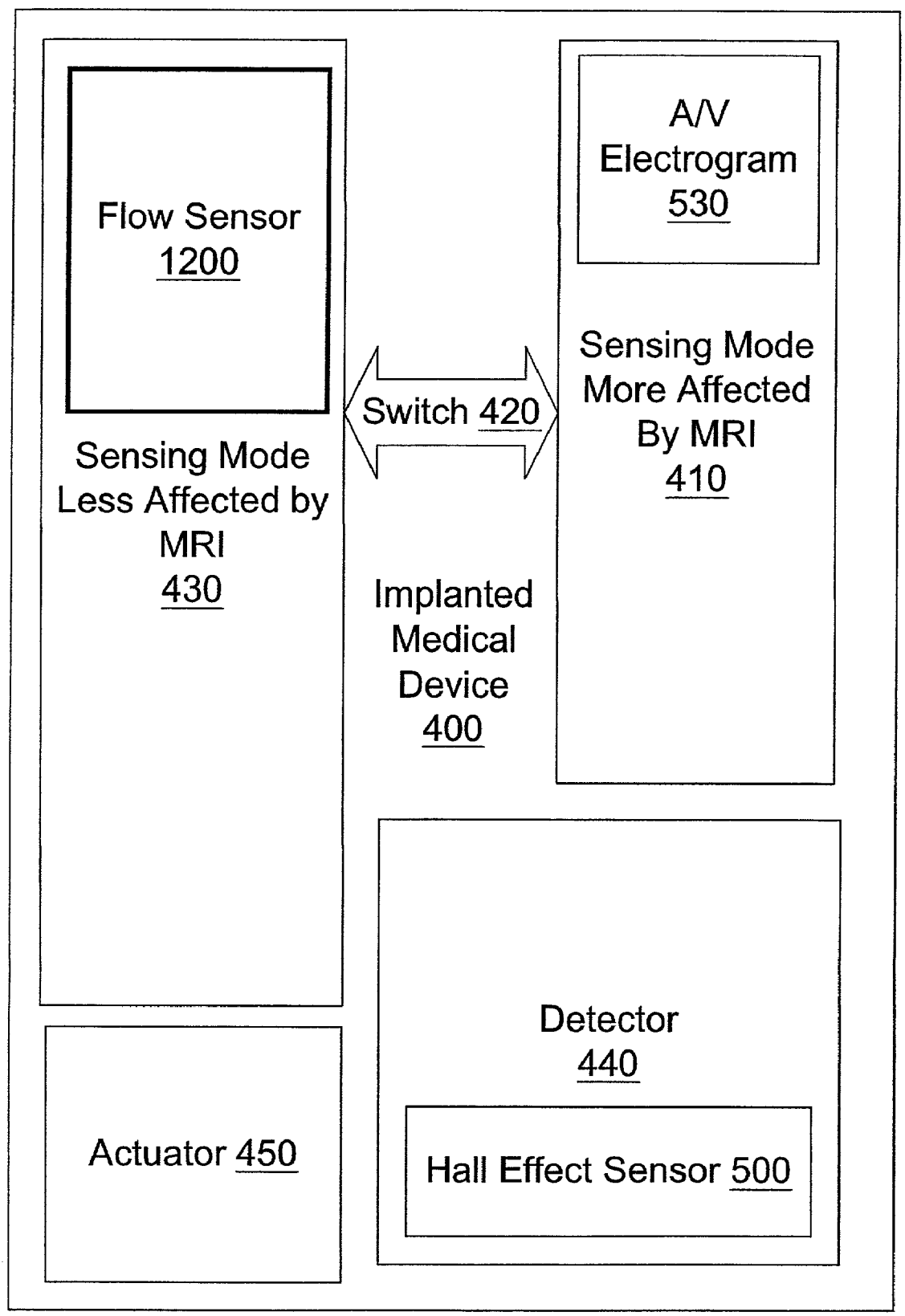
Figure 13:
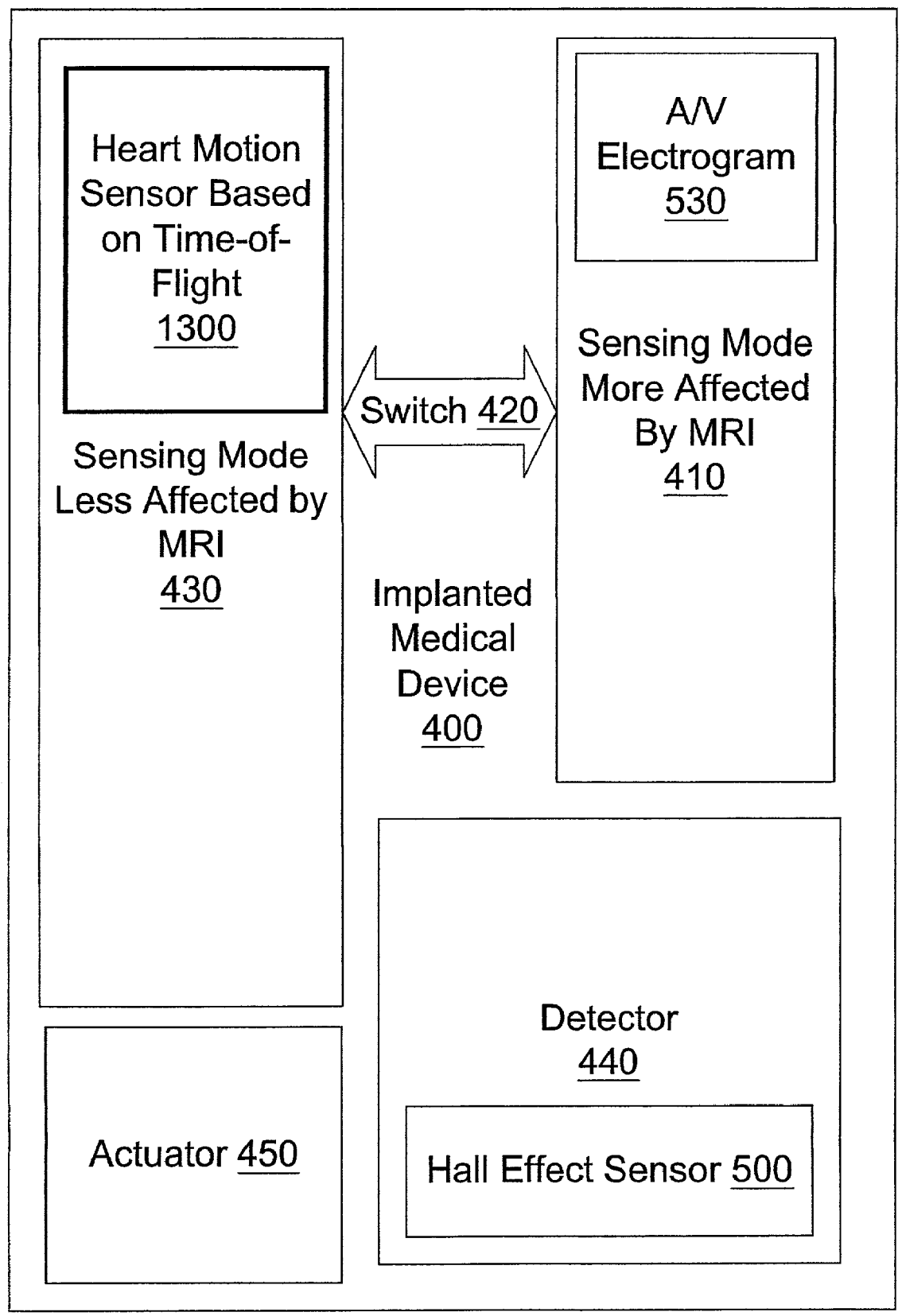
Figure 14:
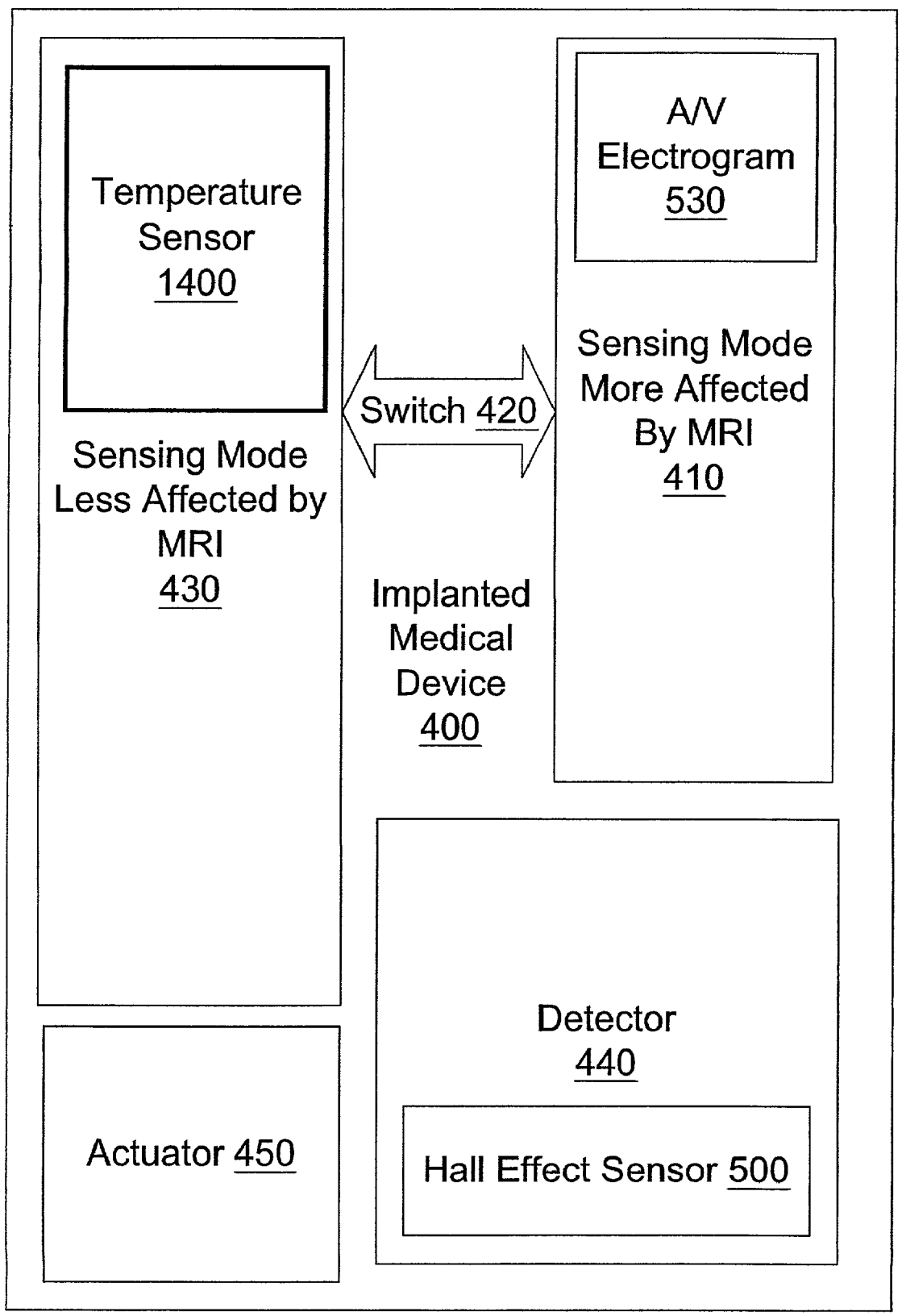
Figure 15:
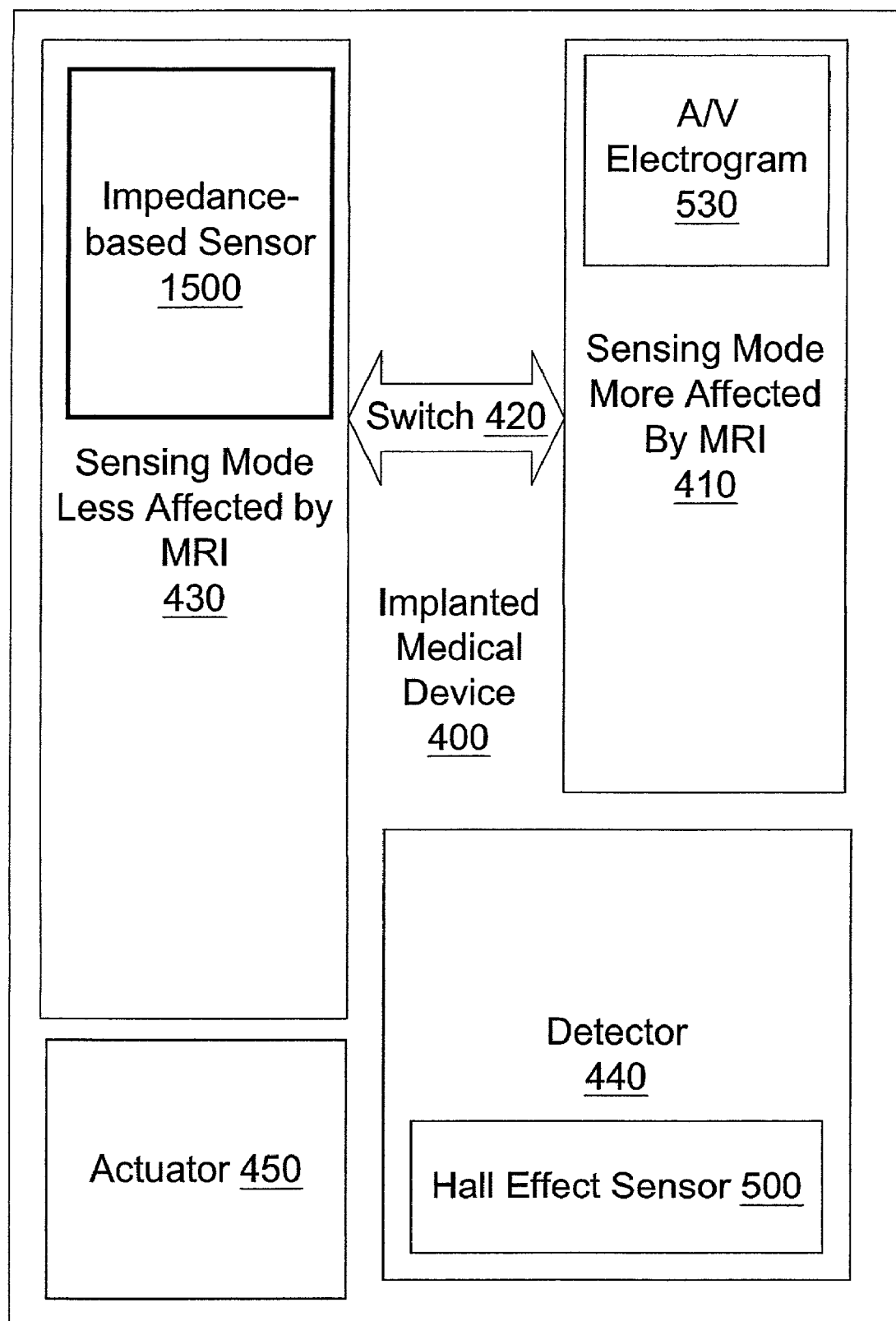
Figure 16:
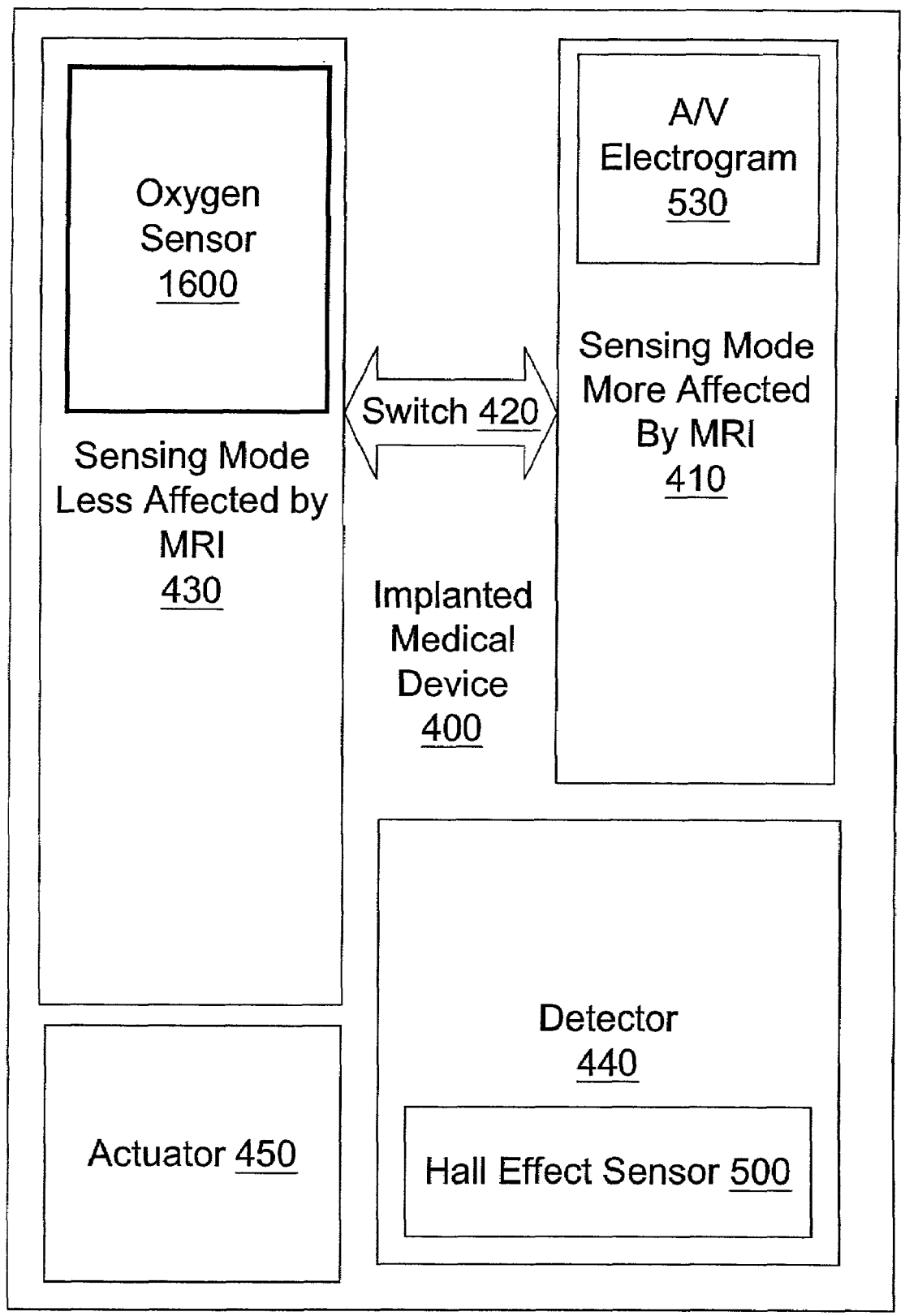

For example, a low-frequency accelerometer placed on the sternum (chest wall) can produce a good signal related to the chest wall vibration due to the heart motion. Such a low-frequency accelerometer placed on the sternum has been used to correlate the cardiac function, including cardiac rhythm, as described, for example, in U.S. Pat. No. D338,272 to Cunagin et al., U.S. Pat. No. 5,159,932 to Zanetti et al., and U.S. Pat. No. 4,989,611 to Zanetti et al., hereby incorporated by reference herein in their entireties. As shown in FIG. 8, the can-based accelerometer 800 can similarly be used to assess the cardiac rhythm during a magnetic resonance imaging (MRI) scan when the normal electrical senseamplifier sensing operation is impaired due to interference from the magnetic resonance imaging (MRI) scan.

For another example, a blood pressure sensor on a lead may be used to sense changes in blood pressure and temperature related to changes in cardiac pacing as described, for example, in U.S. Pat. No. 6,234,973 to Meador et al., and U.S. Pat. No. 5,904,708 to Goedeke, hereby incorporated by reference herein in their entireties. For yet another example, a blood flow sensor positioned in the atrial tract near the heart may be used to assess cardiac function, as described, for example, in U.S. Pat. No. 5,989,192 to Weijand, et al., hereby incorporated by reference herein in its entirety. For yet another example, an impedance sensor may be used to sense changes in patient respiration related to cardiac function, as described, for example, in U.S. Pat. No. 5,836,975, hereby incorporated by reference herein in its entirety.

In an alternative embodiment, the A/V electrogram 600 may itself be adapted to enter a second sensing mode that may allow the A/V electrogram 600 to continue sensing in the presence of interference from magnetic resonance imaging devices.

Figure 18:
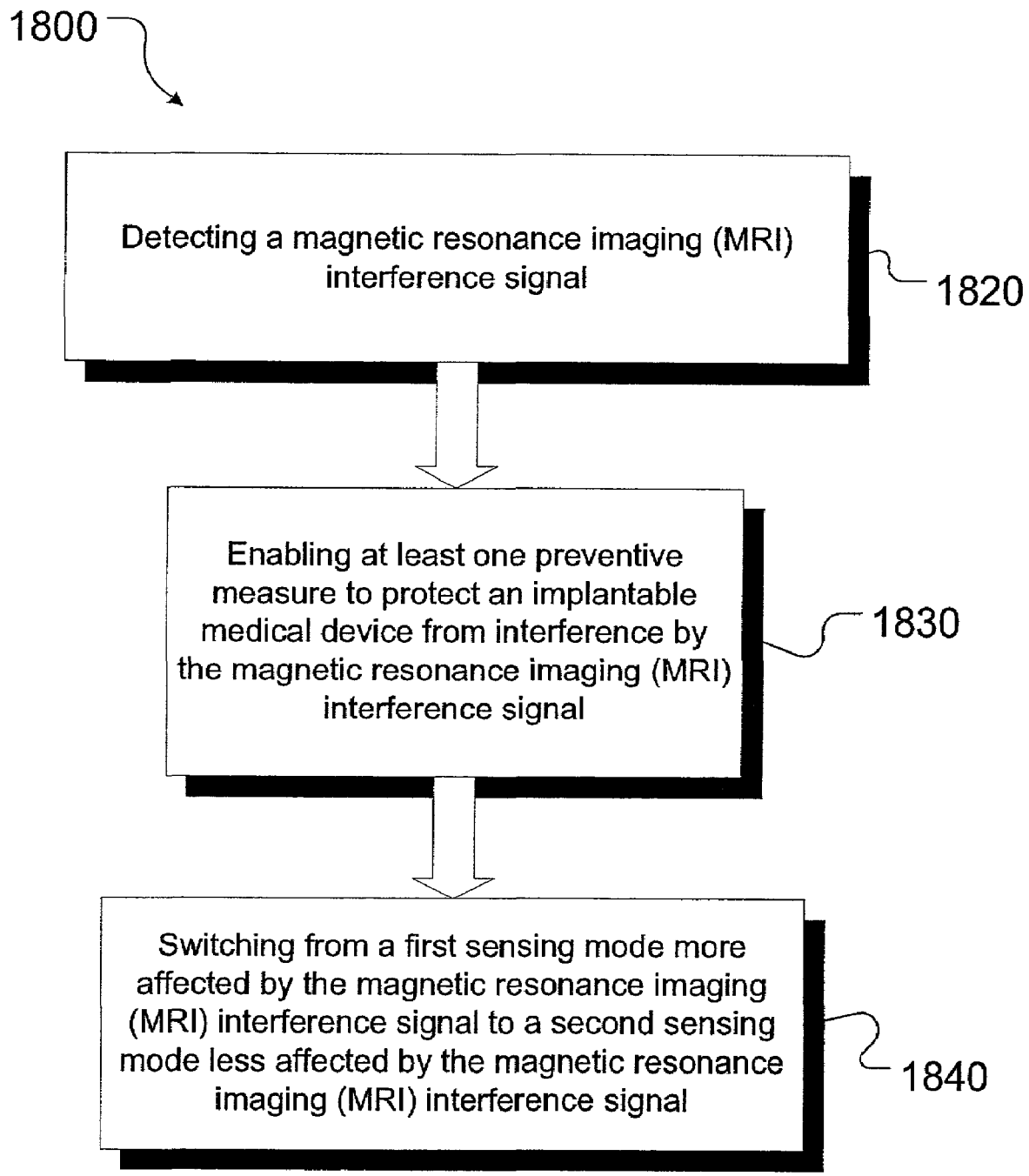
Figure 19:
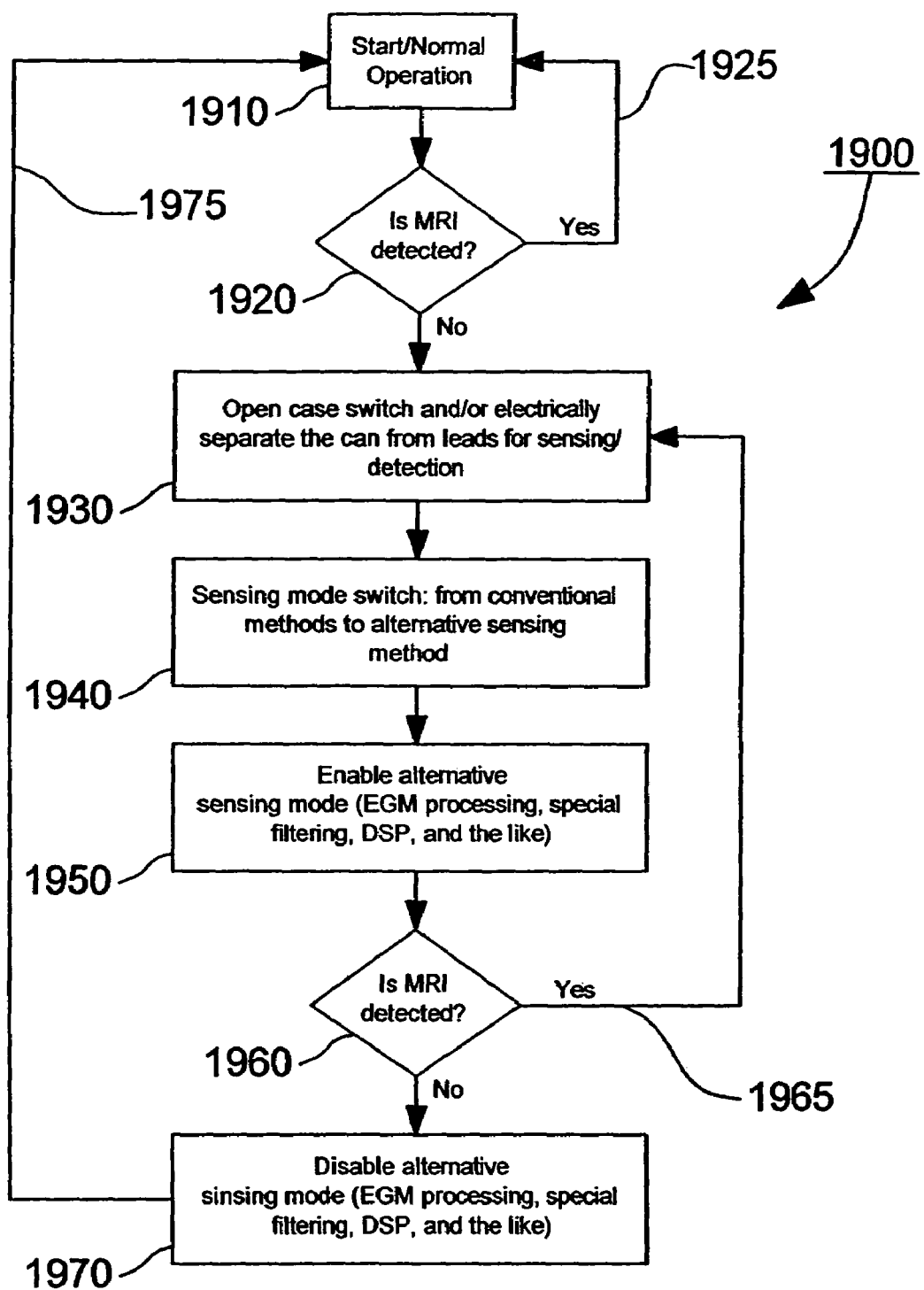

FIGS. 18 and 19 schematically illustrate particular embodiments of respective methods 1800 and 1900 practiced in accordance with the present invention. FIGS. 1–17 schematically illustrate various exemplary particular embodiments with which the methods 1800 and 1900 may be practiced. For the sake of clarity, and to further an understanding of the invention, the methods 1800 and 1900 shall be disclosed in the context of the various exemplary particular embodiments shown in FIGS. 1–17. However, the present invention is not so limited and admits wide variation, as is discussed further below.

As shown in FIG. 18, the method 1800 begins, as set forth in box 1820, by detecting a magnetic resonance imaging (MRI) interference signal. For example, as shown in FIG. 5, in various illustrative embodiments, the detector 440 may use a Hall Effect sensor 500 to detect the high magnetic field associated with a magnetic resonance imaging (MRI) scan.

The method 1800 proceeds by enabling at least one preventive measure to protect an implantable medical device from interference by the magnetic resonance imaging (MRI) interference signal, as set forth in box 1830. For example, in various illustrative embodiments, the actuator 450 capable of enabling at least one preventive measure to protect the implantable medical device 400 from interference by the magnetic resonance imaging (MRI) interference signal may be capable of opening the case switch 610 for the implantable medical device 400. Alternatively, and/or additionally, as shown in FIG. 7, in various illustrative embodiments, the actuator 450 capable of enabling at least one preventive measure to protect the implantable medical device 400 from interference by the magnetic resonance imaging (MRI) interference signal may be capable of electrically isolating one or more of the leads 114 from the can 113 (FIG. 1) using the lead isolator 700, for example.

The method 1800 then proceeds, as set forth in box 1840, by switching from a first sensing mode more affected by the magnetic resonance imaging (MRI) interference signal to a second sensing mode less affected by the magnetic resonance imaging (MRI) interference signal. For example, in various illustrative embodiments, the switch 420 may switch from the first sensing mode 410 more affected by the magnetic resonance imaging (MRI) interference signal to the second sensing mode 430 less affected by the magnetic resonance imaging (MRI) interference signal.

As shown in FIG. 6, the first sensing mode 410 more affected by the magnetic resonance imaging (MRI) interference signal may use the conventional atrial/ventricular electrogram (A/V electrogram) 600 measuring voltages, and/or another type of conventional mechanism for measuring voltages, and for sensing and evaluating basic cardiac rhythms. As shown in FIGS. 8–17, the second sensing mode 430 less affected by the magnetic resonance imaging (MRI) interference signal may use one or more of the can-based accelerometer 800, the pressure sensor on a lead 900, the accelerometer on a lead 1000, the accelerometer on a connector block 1100, the flow sensor 1200, the heart motion sensor 1300 based on time-of-flight, a temperature sensor 1400, the impedance-based sensor 1500 and/or the oxygen sensor 1600, each indicated in phantom in FIG. 17, substantially simultaneously and/or sequentially as appropriate, for basic cardiac rhythm sensing and/or to assess cardiac rhythm(s). In an alternative embodiment, the A/V electrogram 600 may itself be adapted to enter a second sensing mode that may allow the A/V electrogram 600 to continue sensing in the presence of interference from magnetic resonance imaging devices.

As shown in FIG. 19, the method 1900 begins, as set forth in box 1910, by starting and/or continuing normal operations. Then, as shown by decision node 1920, the method 1900 proceeds by addressing the question of whether or not a magnetic resonance imaging (MRI) scan environment is detected. If no magnetic resonance imaging (MRI) scan environment is detected, the method 1900 proceeds by returning to the normal operations of box 1910 along path 1925. However, if a magnetic resonance imaging (MRI) scan environment is detected, the method 1900 proceeds by opening the case switch 610 and/or electrically separating the can 113 from one or more of the leads 114 for sensing/detection, as set forth in box 1930, by using the lead isolator 700, for example.

The method 1900 proceeds by switching the sensing mode, as set forth in box 1940, using the switch 420, for example, from the conventional sensing/detecting mode 410 to the alternative sensing/detecting mode 430, which may be any of the methods discussed above. The method 1900 then proceeds by enabling (MRI) sensing/detecting mode 430, as set forth in box 1950, using one or more of electrocardiogram (EGM) processing, special filtering, digital signal processing (DSP), and the like.

As shown by decision node 1960, the method 1900 then proceeds by addressing the question again of whether or not a magnetic resonance imaging (MRI) scan environment is detected. If the magnetic resonance imaging (MRI) scan environment is still detected, the method 1900 proceeds by returning to the box 1930 along path 1965. However, if no magnetic resonance imaging (MRI) scan environment is detected, the method 1900 proceeds, as set forth in box 1970, by disabling the alternative magnetic resonance imaging (MRI) sensing/detecting mode 430 using one or more of electrocardiogram (EGM) processing, special filtering, digital signal processing (DSP), and the like. The method 1900 proceeds by returning to the normal operations of box 1910 along path 1975, returning to the original parameter/sensing settings.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. In particular, every range of values (of the form, "from about a to about b," or, equivalently, "from approximately a to b," or, equivalently, "from approximately a–b") disclosed herein is to be understood as referring to the power set (the set of all subsets) of the respective range of values. Accordingly, the protection sought herein is as set forth in the claims below.

What is claimed:

1. A device adapted to perform a cardiac sensing-mode switch so to sense cardiac activity in the presence of magnetic resonance imaging (MRI) interference that exceeds a threshold of about 0.20 Tesla but not to perform said mode switch in the presence of electromagnetic interference (EMI) that does not exceed a threshold of about 0.20 Tesla, comprising:
   means for detecting a magnetic field consistent with the characteristics of an MRI scanning device and providing an MRI interference signal related to the detection of the magnetic field; and
   switching means coupled to the means for detecting, for switching from a first cardiac activity sensing mode that is relatively more affected by the MRI interference signal to a second cardiac activity sensing mode that is relatively less affected by the magnetic field in response to receipt of the MRI interference signal, wherein in the event that a detected EMI field strength falls below about 0.20 Tesla then no switching of the first cardiac activity sensing mode occurs;
wherein the second cardiac activity sensing mode employs at least one of the following cardiac activity sensing circuitry disposed within an implantable medical device;
   a can-based accelerometer, a pressure sensor on a lead, an accelerometer on a lead, an accelerometer coupled to a connector block a flow sensor, a heart motion sensor based on time-of-flight, a temperature sensor, an impedance-based sensor, an oxygen sensor.

2. The device of claim 1, wherein the means for detecting is capable of detecting the magnetic field by detecting a high magnetic field having a magnetic field strength above a predetermined threshold other than about 0.17 Tesla.

3. The device of claim 2, wherein the predetermined threshold is about 0.20 Tesla.

4. The device of claim 2, wherein the means for detecting is capable of detecting the magnetic field by detecting the high magnetic field using a Hall Effect sensor in communication with the implantable medical device.

5. The device of claim 4, further comprising means for opening a case switch for the implantable medical device in response to receipt of the MRI interference signal.

6. The device of claim 5, further comprising means for electrically separating one or more leads for the implantable medical device from a portion of a housing for the implantable medical device in response to receipt of the MRI interference signal.

7. A device according to claim 1, wherein means for detecting the magnetic field comprises detecting a high magnetic field having a magnetic field strength of about 0.2 Tesla (2000 Gauss) to about 10 Tesla (100,000 Gauss).

8. A device according to claim 1, wherein the means for detecting the magnetic field comprises detecting a high magnetic field having one of: a static gradient magnetic field, a variable gradient magnetic field with a frequency of about 5 KHz, a radio-frequency pulses of up about 10 MHz to about 50 MHz, a variable magnetic field having a frequency of about 64 Hz.

* * * * *

UNITED STATES PATENT AND TRADEMARK OFFICE
CERTIFICATE OF CORRECTION

PATENT NO. : 7,076,283 B2 Page 1 of 1
APPLICATION NO. : 10/004237
DATED : July 11, 2006
INVENTOR(S) : Yong Kyun Cho et al.

It is certified that error appears in the above-identified patent and that said Letters Patent is hereby corrected as shown below:

Title page item (54) Title to read as follows: --ALTERNATIVE SENSING METHOD FOR IMPLANTABLE MEDICAL DEVICE IN MAGNETIC RESONANCE IMAGING DEVICE--

Signed and Sealed this

Fifth Day of June, 2007

JON W. DUDAS
*Director of the United States Patent and Trademark Office*